United States Patent
Deuel et al.

(10) Patent No.: US 12,376,844 B2
(45) Date of Patent: Aug. 5, 2025

(54) SUTURE BASED CLOSURE DEVICE

(71) Applicant: BOSTON SCIENTIFIC SCIMED, INC., Maple Grove, MN (US)

(72) Inventors: Christopher R. Deuel, Melrose, MA (US); Kevin L. Bagley, Natick, MA (US); Stan Robert Gilbert, Litchfield, NH (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 581 days.

(21) Appl. No.: 17/729,741

(22) Filed: Apr. 26, 2022

(65) Prior Publication Data
US 2022/0338862 A1 Oct. 27, 2022

Related U.S. Application Data

(60) Provisional application No. 63/179,948, filed on Apr. 26, 2021.

(51) Int. Cl.
| | |
|---|---|
| *A61B 17/04* | (2006.01) |
| *A61B 1/00* | (2006.01) |
| *A61B 17/00* | (2006.01) |
| *A61B 17/08* | (2006.01) |

(52) U.S. Cl.
CPC ...... *A61B 17/0469* (2013.01); *A61B 1/00101* (2013.01); *A61B 2017/00296* (2013.01); *A61B 2017/00367* (2013.01); *A61B 2017/081* (2013.01)

(58) Field of Classification Search
CPC ............ A61B 17/0469; A61B 1/00101; A61B 2017/00296; A61B 2017/00367; A61B 2017/081
See application file for complete search history.

(56) References Cited

U.S. PATENT DOCUMENTS

| | | |
|---|---|---|
| 5,478,344 A | 12/1995 | Stone |
| 5,584,861 A | 12/1996 | Swain et al. |
| 6,086,608 A | 7/2000 | Ek et al. |
| (Continued) | | |

FOREIGN PATENT DOCUMENTS

| | | |
|---|---|---|
| CA | 2682488 A1 | 10/2008 |
| DE | 202005022017 U1 | 5/2012 |
| (Continued) | | |

OTHER PUBLICATIONS

International Search Report and Written Opinion dated Aug. 20, 2019 for International Application No. PCT/US2019/033748.
(Continued)

*Primary Examiner* — Brooke Labranche
(74) *Attorney, Agent, or Firm* — Seager, Tufte & Wickhem, LLP

(57) ABSTRACT

A medical device includes a mounting structure that is adapted to be secured to a distal end of an endoscope. A first suture arm is pivotably secured to the mounting structure and is adapted to releasably secure a needle that is adapted to puncture tissue while accommodating a suture. A second suture arm is pivotably secured to the mounting structure and is adapted to releasably secure the needle. The first suture arm and the second suture arm cooperate to pass the needle back and forth therebetween along an arcuate path.

20 Claims, 16 Drawing Sheets

(56) References Cited

U.S. PATENT DOCUMENTS

| | | |
|---|---|---|
| 6,200,329 B1 | 3/2001 | Fung et al. |
| 6,494,888 B1 | 12/2002 | Laufer et al. |
| 6,506,196 B1 | 1/2003 | Laufer |
| 6,554,845 B1 | 4/2003 | Fleenor et al. |
| 6,569,085 B2 | 5/2003 | Kortenbach et al. |
| 6,626,917 B1 | 9/2003 | Craig |
| 6,663,639 B1 | 12/2003 | Laufer et al. |
| 6,719,763 B2 | 4/2004 | Chung et al. |
| 6,740,030 B2 | 5/2004 | Martone et al. |
| 6,746,457 B2 | 6/2004 | Dana et al. |
| 6,755,843 B2 | 6/2004 | Chung et al. |
| 6,773,441 B1 | 8/2004 | Laufer et al. |
| 6,808,491 B2 | 10/2004 | Kortenbach et al. |
| 6,821,285 B2 | 11/2004 | Laufer et al. |
| 6,835,200 B2 | 12/2004 | Laufer et al. |
| 6,908,427 B2 | 6/2005 | Fleener et al. |
| 6,997,931 B2 | 2/2006 | Sauer et al. |
| 7,056,284 B2 | 6/2006 | Martone et al. |
| 7,063,710 B2 | 6/2006 | Takamoto et al. |
| 7,063,715 B2 | 6/2006 | Onuki et al. |
| 7,094,246 B2 | 8/2006 | Anderson et al. |
| 7,144,401 B2 | 12/2006 | Yamamoto et al. |
| 7,147,646 B2 | 12/2006 | Dana et al. |
| 7,153,314 B2 | 12/2006 | Laufer et al. |
| 7,220,266 B2 | 5/2007 | Gambale |
| 7,232,445 B2 | 6/2007 | Kortenbach et al. |
| 7,235,086 B2 | 6/2007 | Sauer et al. |
| 7,326,221 B2 | 2/2008 | Sakamoto et al. |
| 7,344,545 B2 | 3/2008 | Takemoto et al. |
| 7,347,863 B2 | 3/2008 | Rothe et al. |
| 7,361,180 B2 | 4/2008 | Saadat et al. |
| 7,530,985 B2 | 5/2009 | Takemoto et al. |
| 7,601,161 B1 | 10/2009 | Nobles et al. |
| 7,618,425 B2 | 11/2009 | Yamamoto et al. |
| 7,713,277 B2 | 5/2010 | Laufer et al. |
| 7,722,633 B2 | 5/2010 | Laufer et al. |
| 7,727,246 B2 | 6/2010 | Sixto, Jr. et al. |
| 7,736,373 B2 | 6/2010 | Laufer et al. |
| 7,776,057 B2 | 8/2010 | Laufer et al. |
| 7,776,066 B2 | 8/2010 | Onuki et al. |
| 7,842,051 B2 | 11/2010 | Dana et al. |
| 7,846,180 B2 | 12/2010 | Cerier |
| 7,857,823 B2 | 12/2010 | Laufer et al. |
| 7,896,893 B2 | 3/2011 | Laufer et al. |
| 7,918,867 B2 | 4/2011 | Dana et al. |
| 7,951,157 B2 | 5/2011 | Gambale |
| 7,992,571 B2 | 8/2011 | Gross et al. |
| 7,993,368 B2 | 8/2011 | Gambale et al. |
| 8,016,840 B2 | 9/2011 | Takemoto et al. |
| 8,021,376 B2 | 9/2011 | Takemoto et al. |
| 8,057,494 B2 | 11/2011 | Laufer et al. |
| 8,062,314 B2 | 11/2011 | Sixto, Jr. et al. |
| 8,066,721 B2 | 11/2011 | Kortenbach et al. |
| 8,105,355 B2 | 1/2012 | Page et al. |
| 8,211,123 B2 | 7/2012 | Gross et al. |
| 8,216,253 B2 | 7/2012 | Saadat et al. |
| 8,226,667 B2 | 7/2012 | Viola et al. |
| 8,277,468 B2 | 10/2012 | Laufer et al. |
| 8,287,554 B2 | 10/2012 | Cerier et al. |
| 8,287,556 B2 | 10/2012 | Gilkey et al. |
| 8,308,765 B2 | 11/2012 | Saadat et al. |
| 8,313,496 B2 | 11/2012 | Sauer et al. |
| 8,361,089 B2 | 1/2013 | Chu |
| 8,388,632 B2 | 3/2013 | Gambale |
| 8,425,555 B2 | 4/2013 | Page et al. |
| 8,454,631 B2 | 6/2013 | Viola et al. |
| 8,480,691 B2 | 7/2013 | Dana et al. |
| 8,540,735 B2 | 9/2013 | Mitelberg et al. |
| 8,551,120 B2 | 10/2013 | Gambale |
| 8,585,720 B2 | 11/2013 | Gross et al. |
| 8,632,553 B2 | 1/2014 | Sakamoto et al. |
| 8,641,728 B2 | 2/2014 | Stokes et al. |
| 8,679,136 B2 | 3/2014 | Mitelberg |
| 8,709,022 B2 | 4/2014 | Stone et al. |
| 8,764,771 B2 | 7/2014 | Chu |
| 8,882,785 B2 | 11/2014 | DiCesare et al. |
| 8,926,634 B2 | 1/2015 | Rothe et al. |
| 8,992,570 B2 | 3/2015 | Gambale et al. |
| 9,011,466 B2 | 4/2015 | Adams et al. |
| 9,089,325 B2 | 7/2015 | Mitelberg et al. |
| 9,125,646 B2 | 9/2015 | Woodard, Jr. et al. |
| 9,198,562 B2 | 12/2015 | Mitelberg et al. |
| 9,320,515 B2 | 4/2016 | Dana et al. |
| 9,486,126 B2 | 11/2016 | West et al. |
| 9,504,465 B2 | 11/2016 | Chu |
| 9,510,817 B2 | 11/2016 | Saadat et al. |
| 9,549,728 B2 | 1/2017 | Chu |
| 9,750,494 B2 | 9/2017 | Gross et al. |
| 9,788,831 B2 | 10/2017 | Mitelberg |
| 9,844,366 B2 | 12/2017 | Woodard, Jr. et al. |
| 9,867,610 B2 | 1/2018 | Mitelberg et al. |
| 10,045,871 B2 | 8/2018 | Saadat et al. |
| 10,143,463 B2 | 12/2018 | Dana et al. |
| 10,194,902 B2 | 2/2019 | Nobles et al. |
| 10,335,142 B2 | 7/2019 | Raybin et al. |
| 2002/0107530 A1 | 8/2002 | Sauer et al. |
| 2003/0181924 A1 | 9/2003 | Yamamoto et al. |
| 2003/0195529 A1 | 10/2003 | Takamoto et al. |
| 2003/0204205 A1 | 10/2003 | Sauer et al. |
| 2004/0002699 A1 | 1/2004 | Ryan et al. |
| 2004/0138706 A1 | 7/2004 | Abrams et al. |
| 2005/0033319 A1 | 2/2005 | Gambale et al. |
| 2005/0250985 A1 | 11/2005 | Saadat et al. |
| 2006/0282094 A1 | 12/2006 | Stokes et al. |
| 2007/0270908 A1 | 11/2007 | Stokes et al. |
| 2008/0086148 A1 | 4/2008 | Baker et al. |
| 2009/0177031 A1 | 7/2009 | Surti et al. |
| 2010/0137681 A1 | 6/2010 | Ewers et al. |
| 2010/0198006 A1 | 8/2010 | Greenburg et al. |
| 2011/0276064 A1 | 11/2011 | Henrichsen et al. |
| 2011/0313433 A1* | 12/2011 | Woodard, Jr. ...... A61B 17/0469 606/145 |
| 2012/0150200 A1 | 6/2012 | Mitelberg |
| 2012/0158023 A1 | 6/2012 | Miltelberg et al. |
| 2012/0271327 A1 | 10/2012 | West et al. |
| 2012/0277768 A1 | 11/2012 | Viola et al. |
| 2013/0096581 A1 | 4/2013 | Gilkey et al. |
| 2013/0304093 A1 | 11/2013 | Serina et al. |
| 2014/0121457 A1 | 5/2014 | Mort et al. |
| 2014/0128668 A1 | 5/2014 | Cox et al. |
| 2015/0126983 A1 | 5/2015 | Alvarado et al. |
| 2015/0142018 A1 | 5/2015 | Sniffin et al. |
| 2016/0045197 A1 | 2/2016 | Mitelberg et al. |
| 2016/0256140 A1* | 9/2016 | Haack ................ A61B 17/282 |
| 2017/0035413 A1 | 2/2017 | Takahashi |
| 2017/0042534 A1 | 2/2017 | Nobles et al. |
| 2017/0086817 A1 | 3/2017 | Mitelberg |
| 2017/0086818 A1 | 3/2017 | Mitelberg |
| 2017/0119371 A1 | 5/2017 | Mims et al. |
| 2017/0319197 A1 | 11/2017 | Gross et al. |
| 2018/0042602 A1 | 2/2018 | Mitelberg et al. |
| 2018/0042603 A1 | 2/2018 | Mitelberg et al. |
| 2018/0153381 A1 | 6/2018 | Wei et al. |
| 2018/0221009 A1 | 8/2018 | Mitelberg et al. |
| 2018/0235604 A1 | 8/2018 | Comee et al. |
| 2018/0344501 A1 | 12/2018 | Saadat et al. |
| 2020/0000457 A1* | 1/2020 | Gorski ............... A61B 17/0469 |

FOREIGN PATENT DOCUMENTS

| | | |
|---|---|---|
| EP | 1354558 A2 | 10/2003 |
| EP | 1520509 A1 | 4/2005 |
| EP | 2108304 A2 | 10/2009 |
| EP | 2515767 A1 | 7/2011 |
| EP | 2889008 A1 | 7/2015 |
| JP | 2003305046 A | 10/2003 |
| NO | 2016200811 A1 | 12/2016 |
| WO | 0101868 A1 | 1/2001 |
| WO | 0189393 A1 | 11/2001 |
| WO | 2008016592 A2 | 2/2008 |
| WO | 2008045376 A2 | 4/2008 |
| WO | 2008098124 A1 | 8/2008 |
| WO | 2010036227 A1 | 4/2010 |
| WO | 2010085793 | 7/2010 |

(56) References Cited

FOREIGN PATENT DOCUMENTS

| WO | 2013022959 A2 | 2/2013 |
|----|---------------|--------|
| WO | 2017044838 A1 | 3/2017 |
| WO | 2017087856 A1 | 5/2017 |
| WO | 2018156603 A1 | 8/2018 |

OTHER PUBLICATIONS

International Search Report and Written Opinion dated Oct. 1, 2019 for International Application No. PCT/US2019/038006.
Invitation to Pay Additional Fees dated Sep. 26, 2019 for International Application No. PCT/US2019/037995.
International Search Report and Written Opinion dated Dec. 6, 2019 for International Application No. PCT/US2019/037995.
International Search Report and Written Opinion dated Nov. 18, 2019 for International Application No. PCT/US2019/049774.
International Search Report and Written Opinion dated Sep. 20, 2019 for International Application No. PCT/US2019/039312.
International Search Report and Written Opinion dated Jun. 17, 2021 for International Application No. PCT/US2021/024855.
Korean Intellectual Property Office, Office Action, KR Application No. 10-2019-7027516, Mar. 29, 2021 (11 pgs).
International Search Report and Written Opinion dated May 22, 2018 for International Application No. PCT/US2018/018982.
International Search Report and Written Opinion dated Aug. 2, 2022 for International Application No. PCT/US2022/026357.

\* cited by examiner

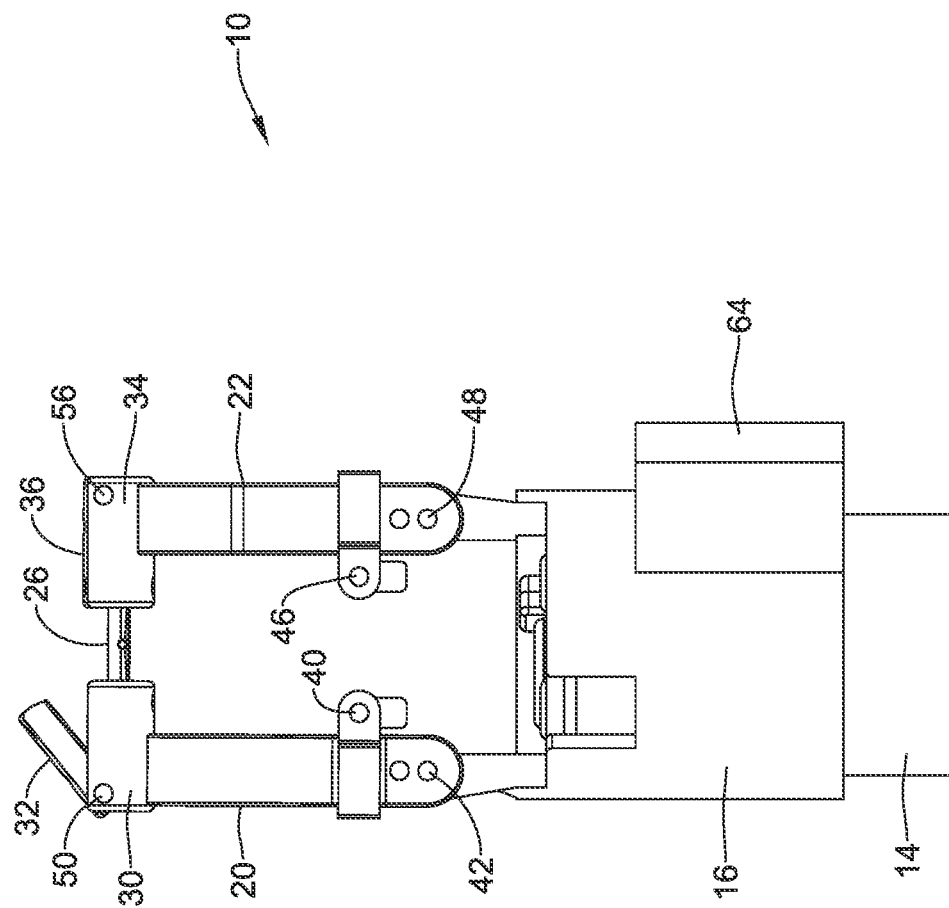

SUTURE BASED CLOSURE DEVICE

CROSS REFERENCE TO RELATED APPLICATIONS

This application claims the benefit of and priority to U.S. Provisional Patent Application Ser. No. 63/179,948 filed on Apr. 26, 2021, the disclosure of which is incorporated herein by reference.

TECHNICAL FIELD

The disclosure is directed to devices for suturing tissue and more particularly to devices that work with an endoscope or similar device for endoscopically suturing tissue.

BACKGROUND

A variety of endoscopic treatments may result in defects (or wounds) that are too large for hemostasis clips to easily bridge and thus help to close the defect. Examples of such endoscopic treatments include removal of large lesions, tunneling under the mucosal layer, full thickness removal of tissue, treating other organs by passing outside of the gastrointestinal tract, and repair of post-surgical issues such as post-surgical leaks, failing surgical staple lines and anastomotic leaks. Endoscopic treatments also include bariatric revision procedures. Of the known devices and methods for endoscopically closing large defects, each has certain advantages and disadvantages.

SUMMARY

The disclosure is directed to several alternative designs, materials and methods of devices for endoscopically closing large defects. In an example, a medical device includes a mounting structure that is adapted to be secured to a distal end of an endoscope. A first suture arm is pivotably secured to the mounting structure via a first pivot point. The first suture arm includes a first latching member at an end of the first suture arm opposing the first pivot point and a first latching feature that is pivotably secured to the first latching member, the first latching feature pivotable between a latching position in which a needle is secured between the first latching member and the first latching feature and a release position. A second suture arm is pivotably secured to the mounting structure via a second pivot point. The second suture arm includes a second latching member at an end of the second suture arm opposing the second pivot point and a second latching feature pivotably secured to the second latching member, the second latching feature pivotable between a latching position in which a needle is secured between the second latching member and a release position.

Alternatively or additionally, the medical device may further include a first control element operably coupled to the first suture arm such that pulling on the first control element causes the first suture arm to move towards the second suture arm and pushing on the first control element causes the first suture arm to move away from the second suture arm.

Alternatively or additionally, the medical device may further include a second control element operably coupled to the second suture arm such that pulling on the second control element causes the second suture arm to move towards the first suture arm and pushing on the second control element causes the second suture arm to move away from the first suture arm.

Alternatively or additionally, the medical device may further include a third control element operably coupled with the first latching feature in order to cause the first latching feature to move between its latching position and its release position and a fourth control element operably coupled with the second latching feature in order to cause the second latching feature to move between its latching position and its release position.

Alternatively or additionally, the medical device may further include a first rounded pin secured to the first latching member and adapted to engage a latching detent of the needle when the needle is disposed between the first latching member and the first latching feature and a second rounded pin secured to the first latching feature and adapted to engage the latching detent of the needle when the first latching feature is in its latching position.

Alternatively or additionally, the first latching member and the first latching feature together may define a first lumen adapted to accept the needle when the first latching feature is in its latching position, and the first rounded pin and the second rounded pin may extend partially into the first lumen.

Alternatively or additionally, the medical device may further include a third rounded pin secured relative to the second latching member and adapted to engage a latching detent of the needle when the needle is disposed between the second latching member and the second latching feature and a fourth rounded pin secured relative to the second latching feature and adapted to engage the latching detent of the needle when the second latching feature is in its latching position.

Alternatively or additionally, the second latching member and the second latching feature in combination may define a second lumen adapted to accept the needle when the second latching feature is in its latching position, and the third rounded pin and the fourth rounded pin may extend partially into the second lumen.

Alternatively or additionally, the first suture arm may be adapted to pivot from a position about 45 degrees from vertical in an outward direction away from the second suture arm to a horizontal position in an inward direction towards the second suture arm.

Alternatively or additionally, the second suture arm may be adapted to permit the first suture arm to pivot through the second suture arm as the first suture arm approaches its horizontal position.

Alternatively or additionally, the second suture arm may be adapted to pivot from a position about 45 degrees from vertical in an outward direction away from the first suture arm to a position about 45 degrees from vertical in an inward direction towards the first suture arm.

In another example, a medical device includes a mounting structure adapted to be secured to a distal end of an endoscope. A first suture arm is pivotably secured to the mounting structure, the first suture arm adapted to releasably secure a needle that is adapted to puncture tissue while accommodating a suture, the first suture arm having a first width. A second suture arm is pivotably secured to the mounting structure, the second suture arm adapted to releasably secure the needle, the second suture arm having a second width greater than the first width such that the first suture arm is able to pivot through the second suture arm in order to capture a newly delivered needle. The first suture arm and the second suture arm are together adapted to pass the needle back and forth therebetween along an arcuate path.

Alternatively or additionally, the first suture arm may be adapted to pivot from a position about 45 degrees from vertical in an outward direction away from the second suture arm to a horizontal position in an inward direction towards the second suture arm.

Alternatively or additionally, the second suture arm may be adapted to pivot from a position about 45 degrees from vertical in an outward direction away from the first suture arm to a position about 45 degrees from vertical in an inward direction towards the second suture arm.

Alternatively or additionally, the medical device may further include a first control element operably coupled to the first suture arm such that pulling on the first control element causes the first suture arm to move towards the second suture arm and pushing on the first control element causes the first suture arm to move away from the second suture arm.

Alternatively or additionally, the medical device may further include a second control element operably coupled to the second suture arm such that pulling on the second control element causes the second suture arm to move towards the first suture arm and pushing on the second control element causes the second suture arm to move away from the first suture arm.

Alternatively or additionally, the medical device may further include a third control element operably coupled with the first latching feature in order to cause the first latching feature to move between its latching position and its release position and a fourth control element operably coupled with the second latching feature in order to cause the second latching feature to move between its latching position and its release position.

In another example, a medical device includes a mounting structure adapted to be secured to a distal end of an endoscope. A first suture arm is pivotably secured to the mounting structure, the first suture arm adapted to releasably secure a needle that is adapted to puncture tissue while accommodating a suture. A second suture arm is pivotably secured to the mounting structure, the second suture arm adapted to releasably secure the needle that is adapted to puncture tissue while accommodating a suture. The first suture arm and the second suture arm are each actuated to move towards each other and to move away from each other in order to pass the needle back and forth therebetween along an arcuate path.

Alternatively or additionally, the first suture arm may include a first latching member and a first latching feature pivotably secured to the first latching member, the first latching feature pivotable between a latching position in which a needle is secured between the first latching member and the first latching feature and a release position.

Alternatively or additionally, the second suture arm may include a second latching member and a second latching feature pivotably secured to the second latching member, the second latching feature pivotable between a latching position in which a needle is secured between the second latching member and the second latching feature and a release position.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which:

FIGS. 7A through 7D are side views of the illustrative assembly of FIG. 1, showing a sequence of events for placing a suture;

Figure 1:
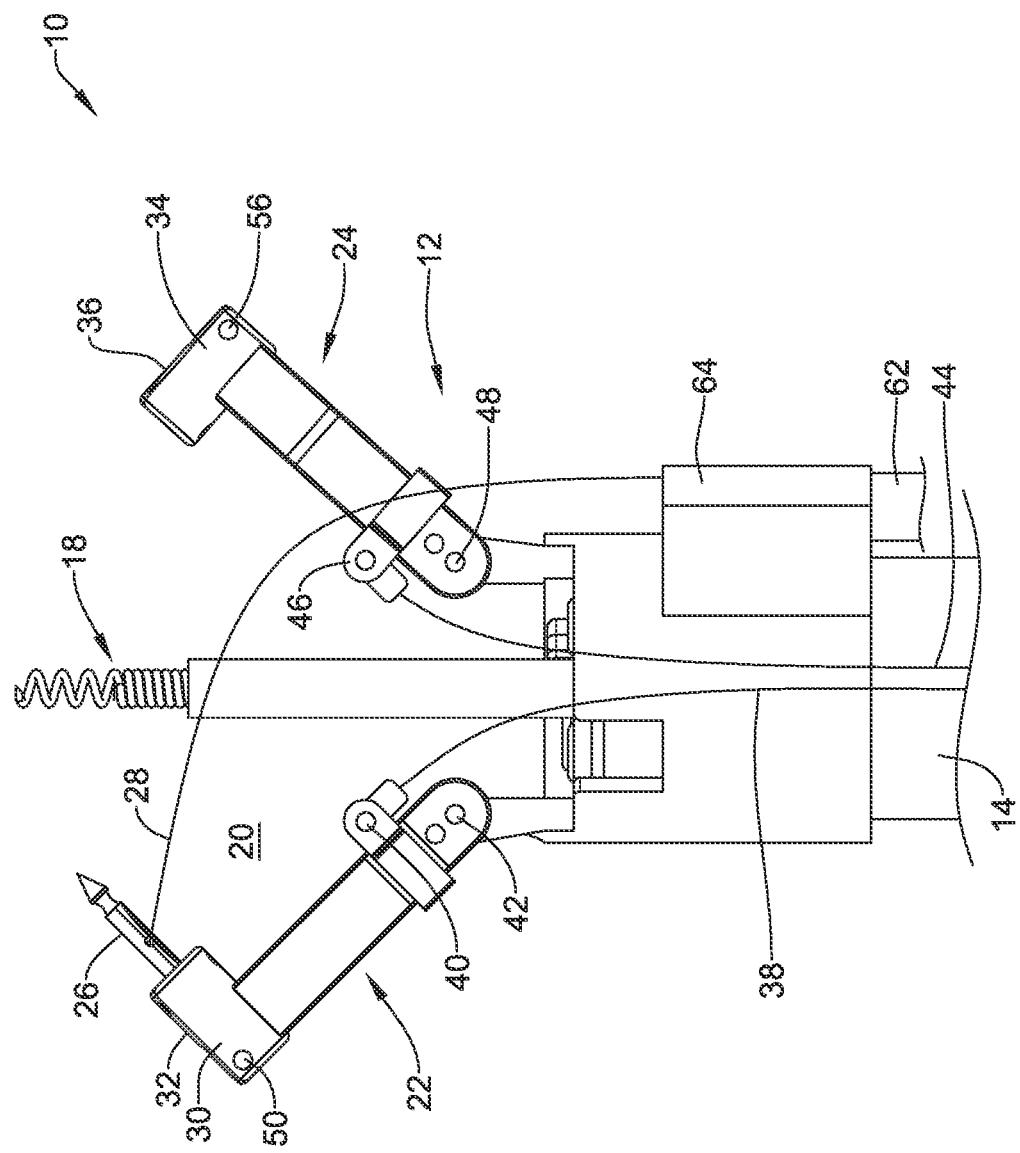
FIG. 1 is a side view of an illustrative assembly including an illustrative suture device secured to a distal end of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure pertains to devices that are configured to be used in combination with an endoscope or a similar delivery device for closing wounds within the body. In some instances, the suture devices described herein may be configured such that they may be used in combination with a single working channel endoscope or a dual working channel endoscope within a single working or available channel of an endoscope, and in some cases may be operated by a single individual, although in some cases a second individual may be involved.

Figure 2:
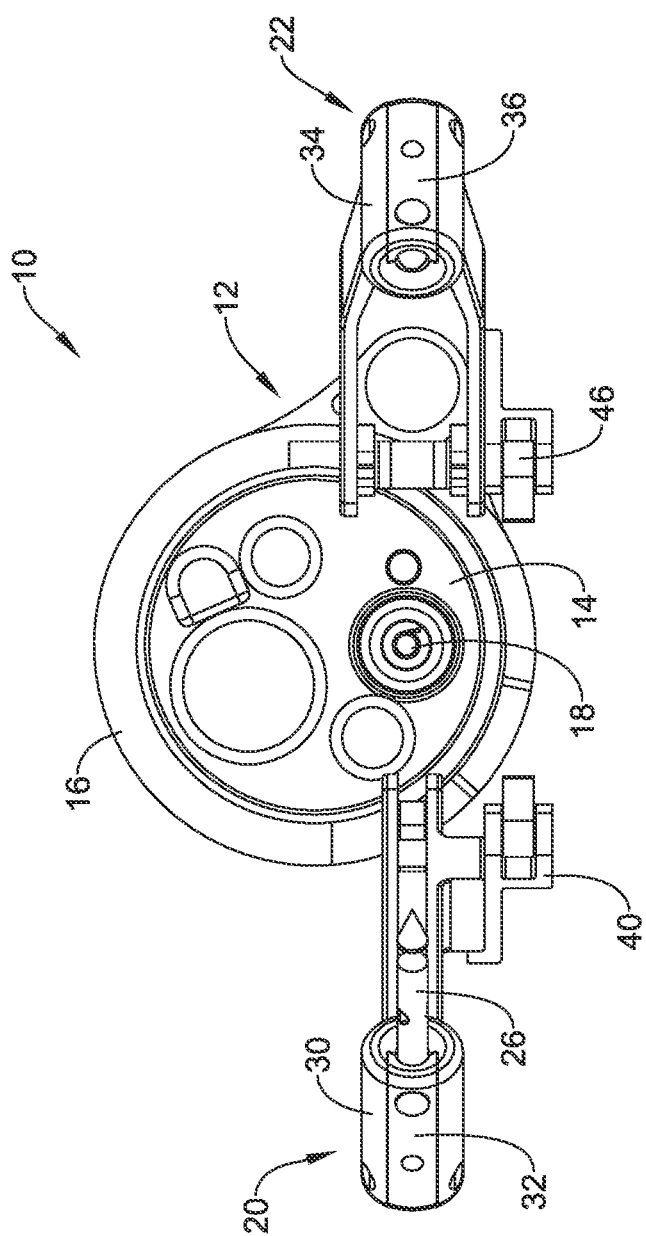
FIG. 2 is an end view of the illustrative assembly of FIG. 1.

FIG. 1 is a perspective view of an illustrative assembly 10 that includes an illustrative suture device 12 secured to a distal end of an endoscope 14 while FIG. 2 is an end view of the illustrative assembly 10. The suture device 12 may be used in combination with a variety of different endoscopes 14, including but not limited to endoscopes 14 that have a primary working channel with a 2.8 millimeter (mm) diameter, a 3.2 mm diameter or a 3.7 mm diameter. It is also understood that the suture device 10 may be used with any of an endoscope, colonoscope, gastroscope, duodenoscope, bronchoscope, uretoscope, catheter, medical device, or the like.

As shown, the illustrative suture device 12 includes an end cap 16 that is configured to secure the suture device 12 relative to the endoscope 14. In general, a first device being adapted to be secured relative to a second device includes the first device being secured directly to the second device and also includes the first device being secured to the second device with one or more intervening structures. For example, the end cap 16 may be any over-the-scope connector. In some instances, the suture device 12 may instead include other structures or features (not illustrated) that are adapted to secure the suture device 12 relative to the endoscope 14. In some cases, as shown, the assembly 10 may include a tissue grasping device 18 that may be used to grasp tissue and pull the tissue into a working space 20 so that the suture device 12 may be used to place one or a plurality of stitches into the tissue. In some embodiments, the tissue grasping device 18 may be a helical device. While the helical tissue grasping device 18 is shown, in some cases other types of graspers may be used, as long as the graspers can fit through the main working channel of the endoscope 14.

The suture device 12 includes a first suture arm 22 and a second suture arm 24 that are configured to be able to pass a needle 26 back and forth between the first suture arm 22 and the second suture arm 24. It will be appreciated that due to the motion of the first suture arm 22 and the second suture arm 24, as will be demonstrated in FIGS. 7A through 7D, the needle 26 may be considered as traveling along an arcuate path. As the needle 26 passes through the tissue, the needle 26 pulls a suture 28 along with the needle 26, thereby pulling the suture 28 through the tissue.

The first suture arm 22 includes a first latching member 30 and a first latching feature 32. The second suture arm 24 includes a second latching member 34 and a second latching feature 36. As will be discussed, the first latching member 30 and the first latching feature 32 work together to releasably secure the needle 26 to the first suture arm 22. Similarly, the second latching member 34 and the second latching feature 36 work together to releasable secure the needle 26 to the second suture arm 24.

In order to cause the first suture arm 22 and the second suture arm 24 to move as desired, the suture device 12 includes a first control element 38 that is attached to a first clevis 40 that is secured to the first suture arm 22 proximate a first pivot point 42. The first control element 38 may be a wire, for example, or other elongate structure having sufficient tensile strength to be able to push or pull the first control element 38. When the first control element 38 is pushed distally, such as by an appropriate handle mechanism (not shown), the first suture arm 22 will be caused to pivot away from the working space 20 and away from the second suture arm 24. When the first control element 38 is pulled proximally, such as by an appropriate handle mechanism (not shown), the first suture arm 22 will be caused to pivot into the working space 20 and towards the second suture arm 24.

The suture device 12 includes a second control element 44 that is attached to a second clevis 46 that is secured to the second suture arm 24 proximate a second pivot point 48. The second control element 44 may be a wire, for example, or other elongate structure having sufficient tensile strength to be able to push or pull the second control element 38. When the second control element 44 is pushed distally, such as by an appropriate handle mechanism (not shown), the second suture arm 22 will be caused to pivot away from the working space 20 and away from the first suture arm 22. When the second control element 44 is pulled proximally, such as by an appropriate handle mechanism (not shown), the second suture arm 24 will be caused to pivot into the working space 20 and towards the second suture arm 22. In some cases, other actuation mechanisms are contemplated, such as the use of one or more gears within the handle mechanism. This is just an example.

The first latching feature 32 is pivotably secured to the first latching member 30 at a pivot point 50. As will be discussed with respect to FIG. 6, a third control element may be used to open and close the first latching feature 32 relative to the first latching member 30. The second latching feature 36 is pivotably secured to the second latching member 34 at a pivot point 56. As will be discussed with respect to FIG. 6, a fourth control element may be used to open and close the second latching feature 36 relative to the second latching member 34.

With particular respect to FIG. 2, it can be seen that the first suture arm 20 and the second suture arm 22 are not identical. Rather, the first suture arm 20 can be seen as being relatively narrow relative to the second suture arm 22, which is wider. This size discrepancy allows the first suture arm 20 to tilt towards the second suture arm 22 and actually fit through the second suture arm 22.

Figure 3:
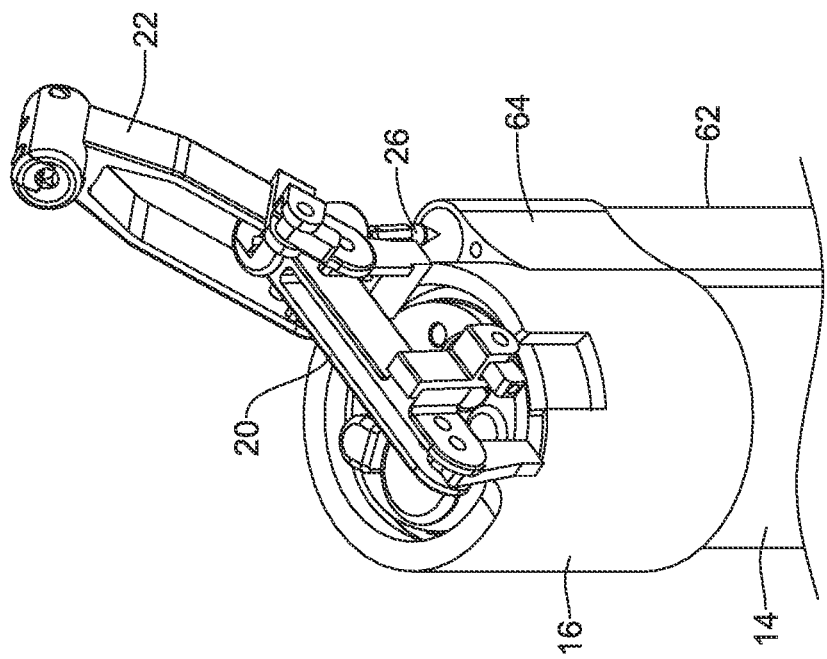
FIG. 3 is a perspective view of the illustrative assembly of FIG. 1, configured for reloading a needle or suture.

FIG. 3 shows the first suture arm 20 in a horizontal or substantially horizontal position in which the first suture arm 20 extends through the second suture arm 22. The first suture arm 20 is in a position to be able to capture the needle 26 as the needle 26 is provided through the external tube 62. This may occur if there is a need to replace the needle 26, for example. In some cases, the needle 26 may be used to terminate a suture, meaning that the needle 26 may be left within the patient's body proximate the tissue being sutured. This may mean that another needle 26 may be needed, if there is another suture to be placed. While in some cases the assembly 10 is advanced towards a suturing site with the needle 26 firmly secured between the first suture arm 20 and the second suture arm 22, in some cases there may be a desire to instead advance the assembly 10 without the needle 26, and only provide the needle 26 once the assembly 10 has reached the suturing site.

As will be appreciated, the first suture arm 20 and the second suture arm 22 are not allowed to freely pivot to any position, but are configured to provide limits on travel. In some cases, for example, the first suture arm 20 may be allowed to pivot from a position about 45 degrees from vertical in an outward direction (roughly the position of the first suture arm 20 shown in FIG. 1) and away from the second suture arm 22 to a horizontal position in an inward direction towards the second suture arm 22 (roughly the position of the first suture arm 20 shown in FIG. 3. The second suture arm 22 may be allowed to pivot form a position about 45 degrees from vertical in an outward direction (roughly the position of the second suture arm 22 in FIG. 1) to a position about 45 degrees from vertical in an inward direction towards the first suture arm 20.

Figure 4:
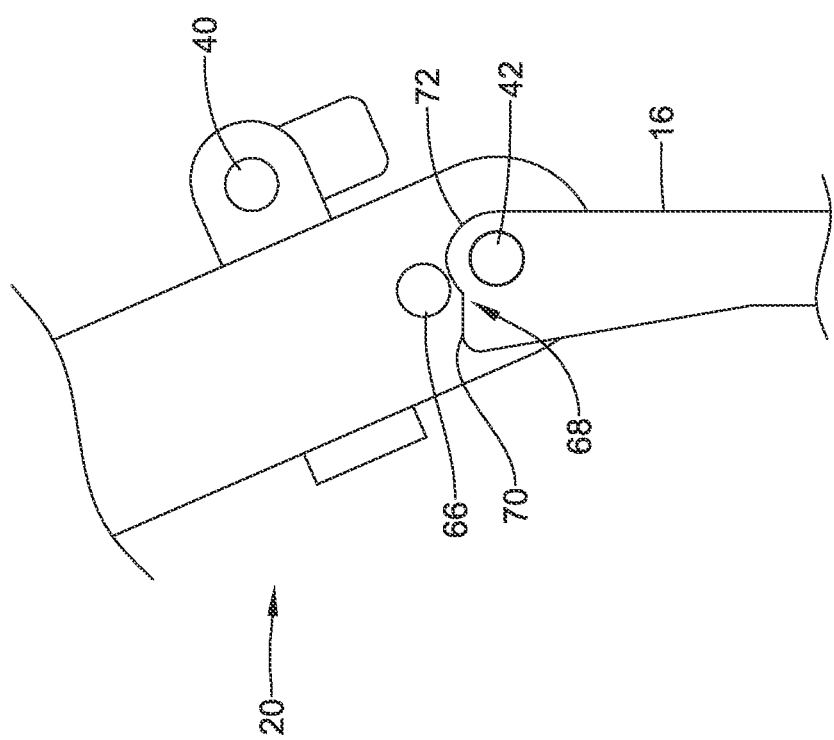
FIG. 4 shows pivot stops formed on one of the suture arms forming a portion of the illustrative assembly of FIG. 1.

The first suture arm 20 and the second suture arm 22 include physical features in order to accomplish these travel limits. FIG. 4 shows a portion of the first suture arm 20 relative to the end cap 16. It can be seen that the first suture arm 20 includes a pivot pin 66 that interacts with a corresponding surface 68 formed on the end cap 16. A portion 70 of the surface 68 can be seen as being configured to limit how far the first suture arm 20 is allowed to pivot in an outward direction, while a portion 72 of the surface 68 is configured to allow the pivot pin 66 to move across the portion 68, allowing the first suture arm 20 to pivot all the way to a horizontal orientation in an inward direction.

Figure 5A:
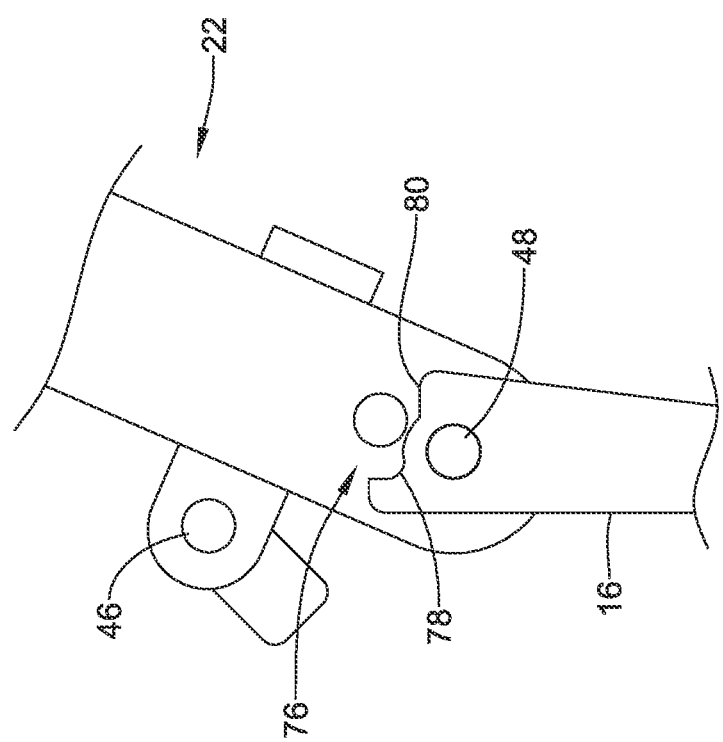
FIGS. 5A and 5B show pivot stops formed on the other of the suture arms forming a portion of the illustrative assembly of FIG. 1.
Figure 5B:
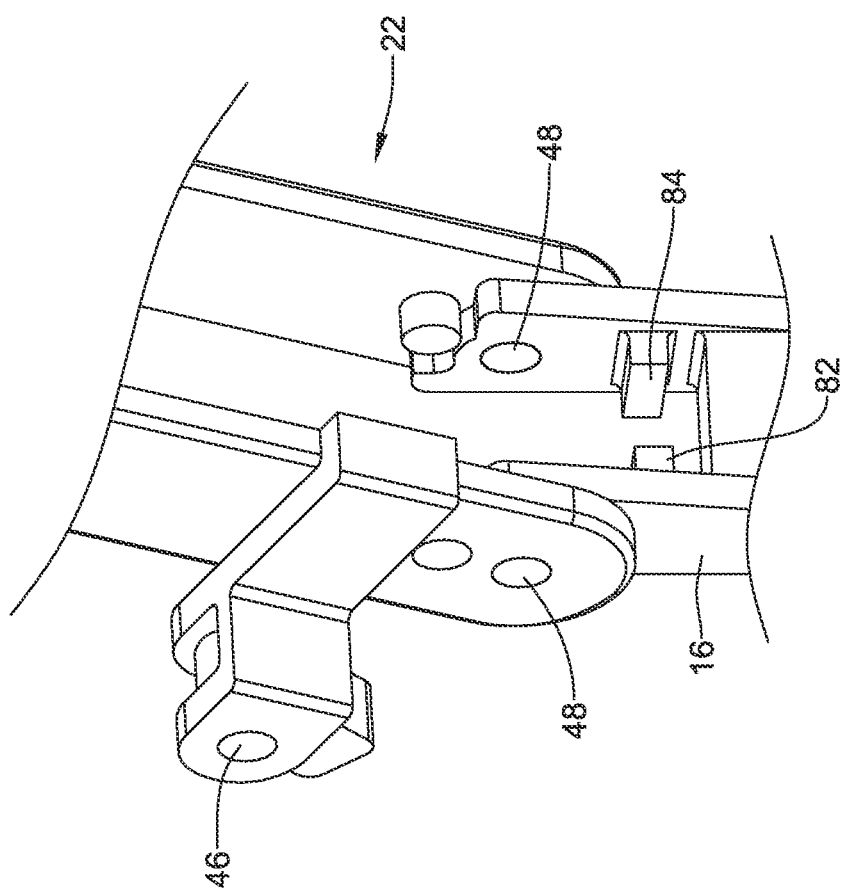

FIGS. 5A and 5B show a portion of the second suture arm 22 relative to the end cap 16. It can be seen that the second suture arm 22 includes a pivot pin 74 that interacts with a corresponding surface 76 formed on the end cap 16. A portion 78 of the surface 76 can be seen as being configured to limit how far the second suture arm 22 is allowed to pivot in an outward direction while a portion 80 of the surface 76 is configured to limit how far the second suture arm 22 is allowed to pivot in an inward direction. As seen in particular in FIG. 5B, the second suture arm 22 includes pivot stops 82 and 84 that prevent the first suture arm 20 from pivoting past a horizontal position.

Figure 6:
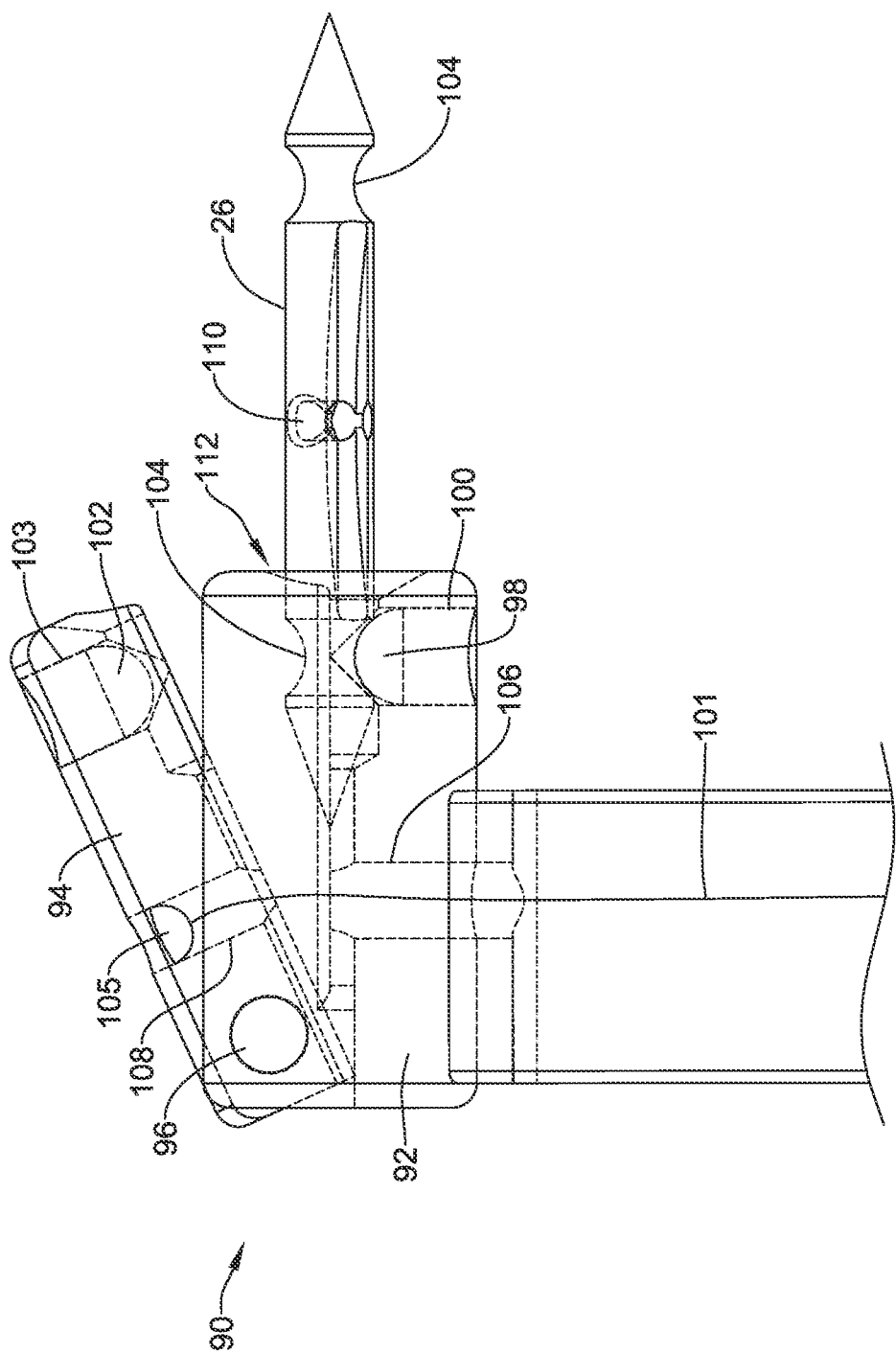
FIG. 6 is a partially cutaway view of an illustrative suture arm forming a portion of the illustrative assembly of FIG. 1.

FIG. 6 is a partial cutaway view of a portion of a suture arm 90 that may be considered as representing either of the first suture arm 20 or the second suture arm 22. The suture arm 90 includes a latching member 92 and a latching feature 94. The latching feature 94 is attached to the latching member 92 via a pivot point 96. It will be appreciated that the latching member 92 may be considered as representing either the first latching member 30 or the second latching member 34 and that the latching feature 94 may be considered as representing either the first latching feature 32 or the second latching feature 36.

A control element 101 extends up through the suture arm 90 and passes through the aperture 106 and into the aperture 108. The control element 101 may be considered as representing either the third control element or the fourth element, depending on whether the suture arm 90 represents the first suture arm 20 or the second suture arm 22. The control element 101 may be a wire, for example, and includes a plug portion 105 that secures the control element 101 within the aperture 108. The plug portion 105 may represent a solder ball, for example, or simply a widened portion of the control element 101 that is frictionally secured within the aperture 108. Pushing the control element 101 may cause the latching feature 94 to open relative to the latching member 94 while pulling the control element 101 may cause the latching feature 94 to close relative to the latching member 94.

The latching member 92 includes a rounded pin 98 that is secured within an aperture 100 formed within the latching member 92. The latching feature 94 includes a rounded pin 102 that is secured within an aperture 103 formed within the latching feature 94. It will be appreciated that the rounded pin 98 and the rounded pin 102 are configured to releasably engage a detent 104 that is formed near either end of the needle 26. When the latching feature 94 is in a closed or latching position (such as the latching features 32, 26 are shown in FIG. 1 or 2), the rounded pins 98 and 102 engage one of the detents 104 to secure the needle 26 relative to the suture arm 90. When the latching feature 94 is in an open or release position (as shown in FIG. 6), the needle 26 is not held in place and thus is released. In some cases, apertures 106 and 108 that are formed within the latching member 92 and the latching feature 94, respectively, allow a control element to pass up to and be secured relative to the latching feature 94. This is not required in all cases, however. It will be appreciated that the needle 26 includes a suture aperture 110 through which a suture such as the suture 28 may be secured.

In comparing FIG. 6 with FIG. 1, it will be appreciated that the suture device 12 may include a first rounded pin that is secured relative to the first latching member 30 and that is adapted to engage a latching detent 104 of the needle 26 when 26 the needle is disposed between the first latching member 30 and the first latching feature 32 as well as a second rounded pin that is secured relative to the first latching feature 32 and adapted to engage the latching detent 104 of the needle 26 when the first latching feature 32 is in its latching position. The first latching member 30 and the first latching feature 32 may be considered as together defining a first lumen (such as a lumen 112 as shown in FIG. 6) that is adapted to accept the needle 26 when the first latching feature 32 is in its latching position, and the first rounded pin and the second rounded pin each extend partially into the first lumen.

The suture device 12 may include a third rounded pin that is secured relative to the second latching member 34 and that is adapted to engage a latching detent 104 of the needle 26 when the needle 26 is disposed between the second latching member 34 and the second latching feature 36 as well as a fourth rounded pin that is secured relative to the second latching feature 36 and is adapted to engage the latching detent 104 of the needle 26 when the second latching feature 36 is in its latching position. The second latching member 34 and the second latching feature 36 may be considered as together defining a second lumen (such as the lumen 112 shown in FIG. 6) that is adapted to accept the needle 26 when the second latching feature 36 is in its latching position, and the third rounded pin and the fourth rounded pin each extend partially into the second lumen.

As an example, the suture device 12 may be secured to the end of the endoscope 14. A needle 26 and suture 28 may be loaded into the suture device 12, with the needle 26 locked into both the first suture arm 20 and the second suture arm 22. The suture 28 extends through the external tubing 62 and the suture device 12 (and endoscope 140 are passed to an area of interest, such as the stomach or the esophagus, for example. In some cases, an over tube (not shown) may be used during intubation in order to protect the patient's esophagus. Once the suture device 12 has been appropriately placed, a tissue grasping device such as but not limited to the helical tissue grasping device 18 may be advanced down a working channel of the endoscope 14. The first suture arm 20 and the second suture arm 22 may be moved into an open position in which the first suture arm 20 and the second suture arm 22 both tilt away from the working space 24 in order to allow for clearance for the tissue grasping device. At this point, the needle 26 remains locked to either the first suture arm 20 or the second suture arm 22. The tissue grasping device may be advanced distally and engages with the tissue. The tissue grasping device may then be pulled proximally in order to pull the tissue into the working space 24. The first suture arm 20 and the second suture arm 22 are rotated towards each other into a closed position in which the needle 26 is able to engage both the first suture arm 20 and the second suture arm 22, thereby forcing the needle 26 and the suture 28 to pass through the tissue. The needle 26 may be transferred from one suture arm to the other by unlocking the suture arm with the needle and locking the arm receiving the needle.

Figure 7A:
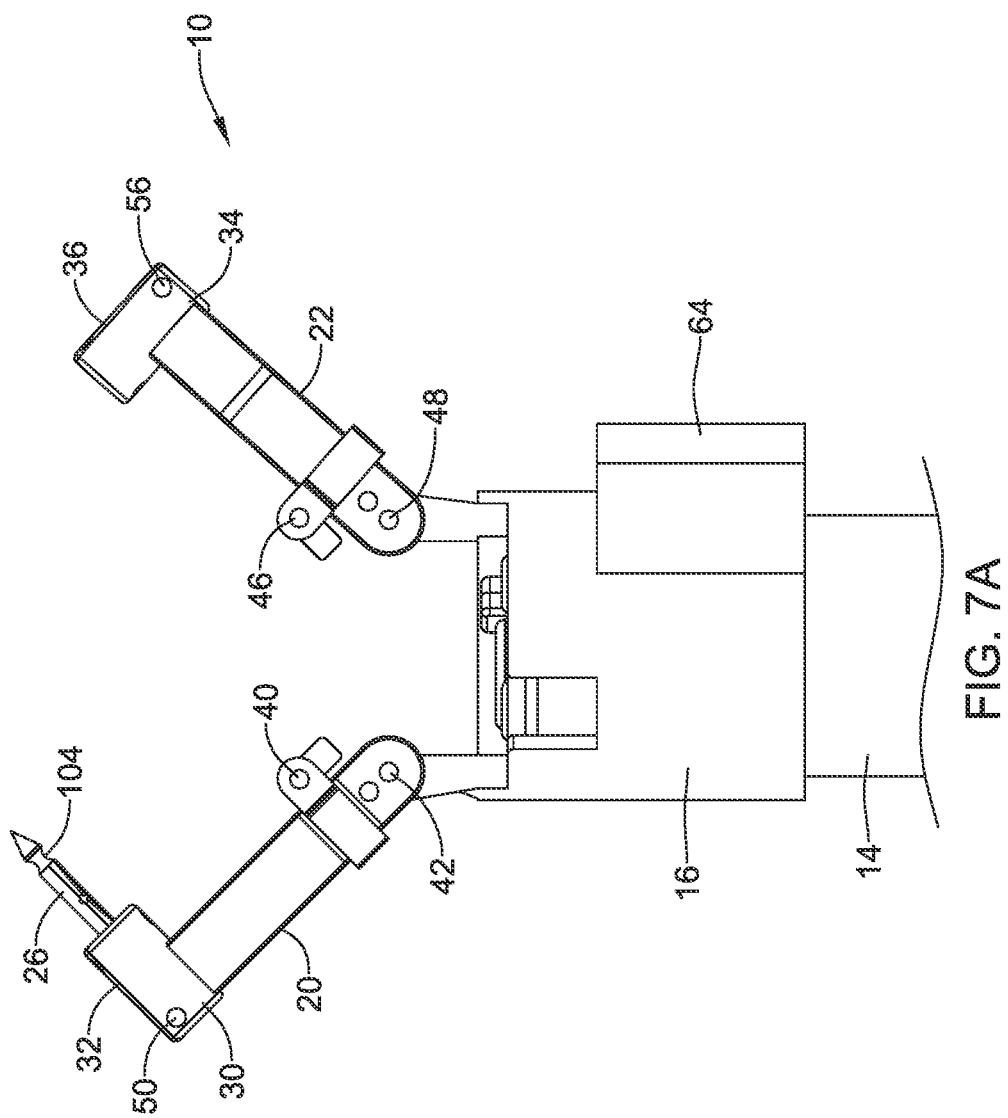
Figure 7B:
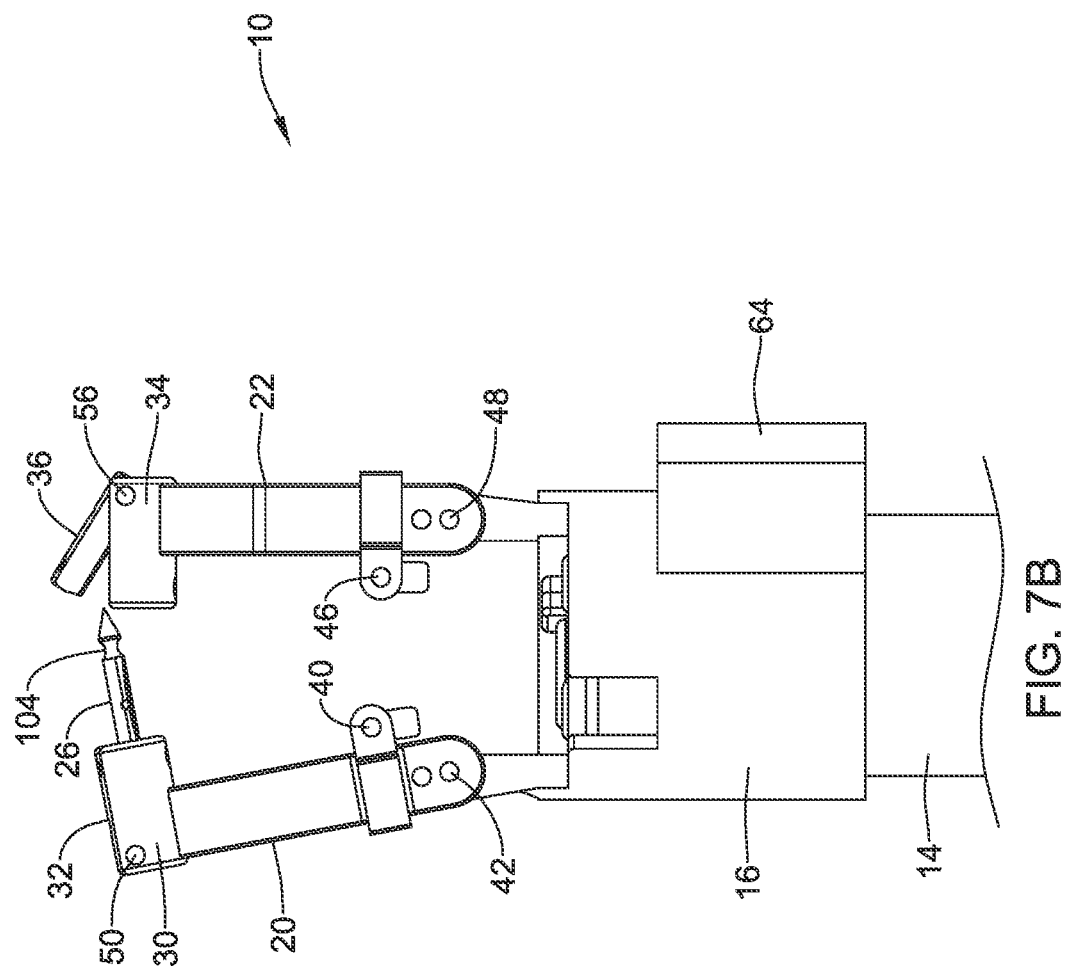

This is illustrated for example in FIGS. 7A through 7D. In FIG. 7A, the needle 26 is locked into the first suture arm 20, and the first suture arm 20 and the second suture arm 20 have been pivoted into an open position in which the first suture arm 20 and the second suture arm 22 tilt away from each other. An unseen tissue grasping device has clearance to grasp tissue and pull the tissue in the working space 24. In FIG. 7B, the first suture arm 20 and the second suture arm 22 have tilted towards each other, and the second latching feature 36 has been opened in order to allow the needle 26 to enter.

Figure 7D:
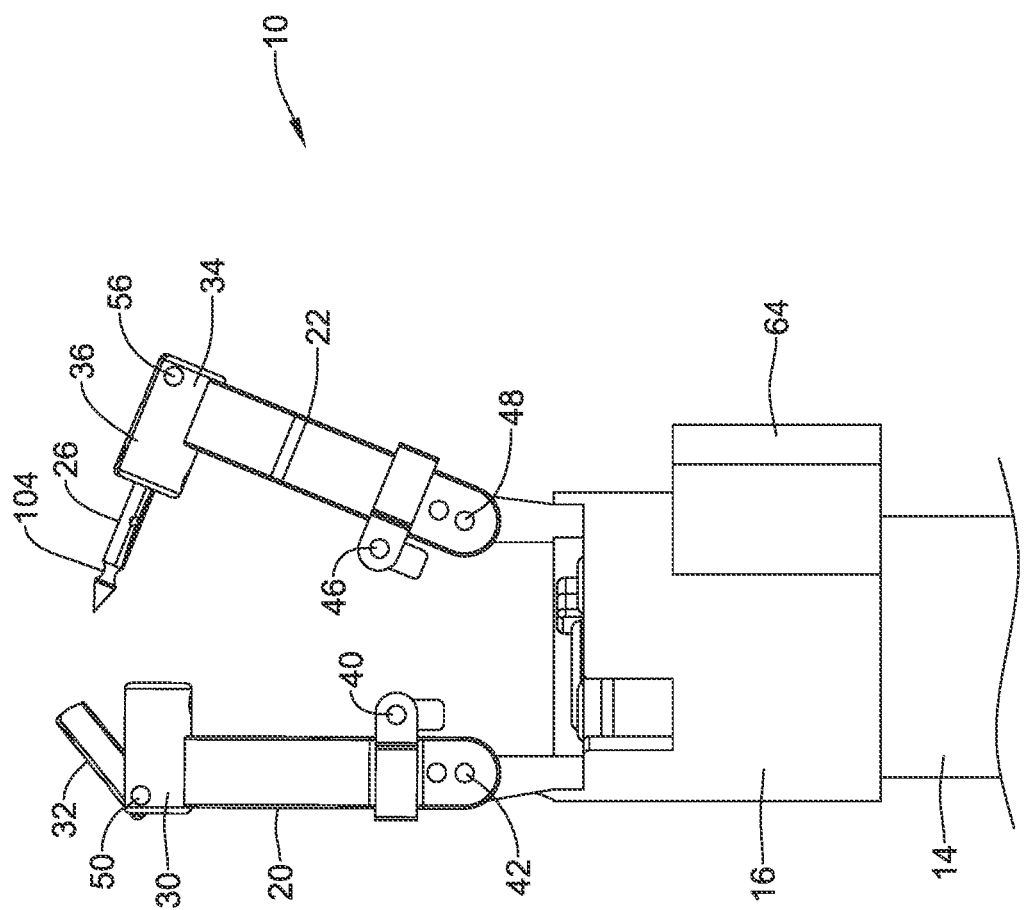

In FIG. 7C, the first suture arm 20 and the second suture arm 22 are in the closed position in which the first suture arm 20 and the second suture arm 22 are roughly parallel with each other. The first latching feature 32 has opened, and the second latching feature 36 has closed. As a result, the needle 26 has been secured relative to the second suture arm 22, and has been released by the second suture arm 22. In FIG. 7D, the second suture arm 22 has tilted away from the first suture arm 20, with the needle 26 secured to the second suture arm 22.

Figure 8:
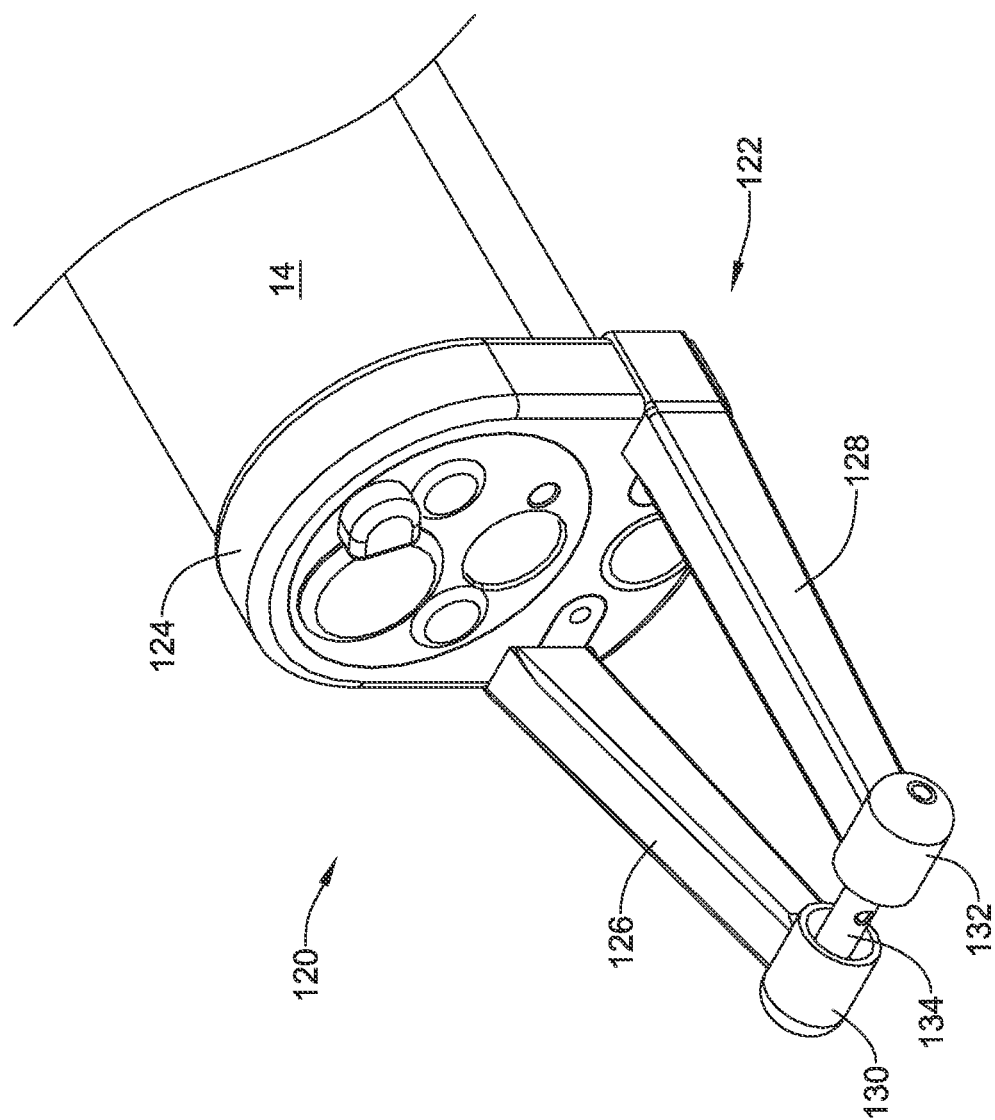
FIG. 8 is a perspective view of an illustrative assembly including an illustrative suture device secured to a distal end of an endoscope.

FIG. 8 is a perspective view of an illustrative assembly 120 that includes an illustrative suture device 122 secured relative to the endoscope 14. The suture device 122 may be used in combination with a variety of different endoscopes 14, including but not limited to endoscopes 14 that have a primary working channel with a 2.8 millimeter (mm) diameter, a 3.2 mm diameter or a 3.7 mm diameter. As shown, the illustrative suture device 122 includes an end cap 124 that is configured to secure the suture device 122 relative to the endoscope 14. For example, the end cap 124 may be any over-the-scope connector. In some instances, the suture device 122 may instead include other structures or features (not illustrated) that are adapted to secure the suture device 122 relative to the endoscope 14.

The suture device 122 includes a first suture arm 126 and a second suture arm 128. The first suture arm 126 includes a first needle receiving feature 130 and the second suture arm 128 includes a second needle receiving feature 132. While not shown, the suture device 122 may include a first control wire extending proximally from the first suture arm 126 and a second control wire extending proximally from the second suture arm 128 so that a user can actuate the first suture arm 126 and the second suture arm 128 as desired. The first suture arm 126 and the second suture arm 128 may lock to a needle 134 via separate control wires that run through the center of each of the suture arms 126, 128 and releasably engage corresponding apertures formed within the needle 134. It will be appreciated that the needle 134 includes a first aperture positioned to receive a wire extending through the first suture arm 126 and a second aperture positioned to receive a wire extending through the second suture arm 128. These apertures are referenced with respect to FIG. 10. The wires that control needle engagement are individually movable, thus the needle 134 can be locked to the first suture arm 126, or locked to the second suture arm 128, or released from either the first suture arm 126 or the second suture arm 128 as desired.

Figure 9:
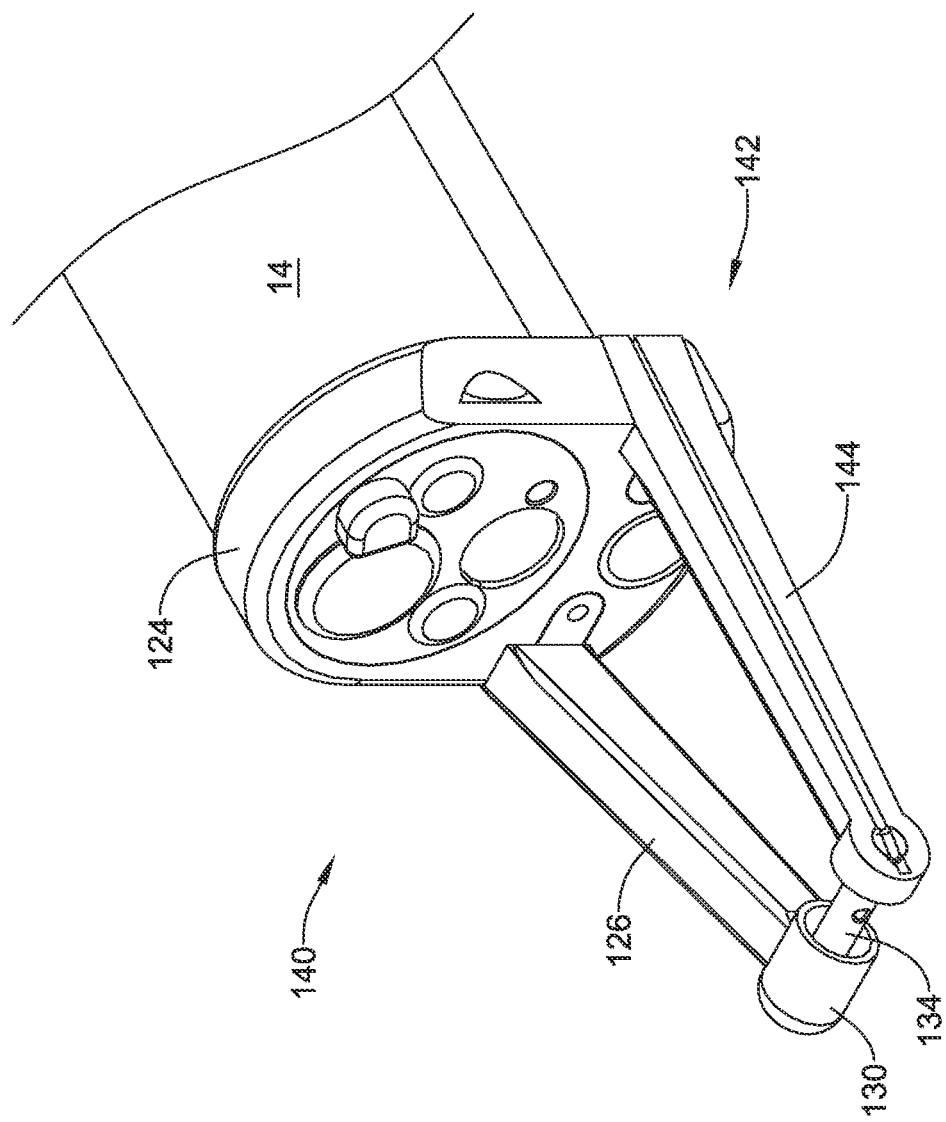
FIG. 9 is a perspective view of an illustrative assembly including an illustrative suture device secured to a distal end of an endoscope.

FIG. 9 is a perspective view of an illustrative assembly 140 that includes an illustrative suture device 142 secured relative to the endoscope 14. The suture device 142 is similar to the suture device 122, but the second suture arm 128 has been replaced with a stationary suture arm 144.

Figure 10:
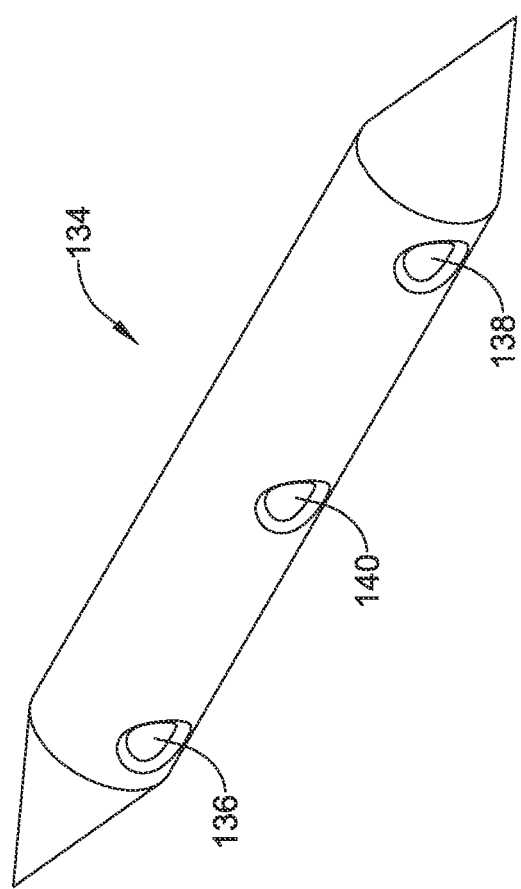
FIG. 10 is a perspective view of a needle usable with the illustrative assemblies of FIGS. 8 and 9.

FIG. 10 is a perspective view of the needle 134. The needle 134 includes a first aperture 136 that is configured to accommodate a wire extending through the first suture arm 126, for example. The needle 134 includes a second aperture 138 that is configured to accommodate a wire extending through the second suture arm 128, for example. A suture aperture 140 permits a suture to be secured to the needle 134.

Figure 11:
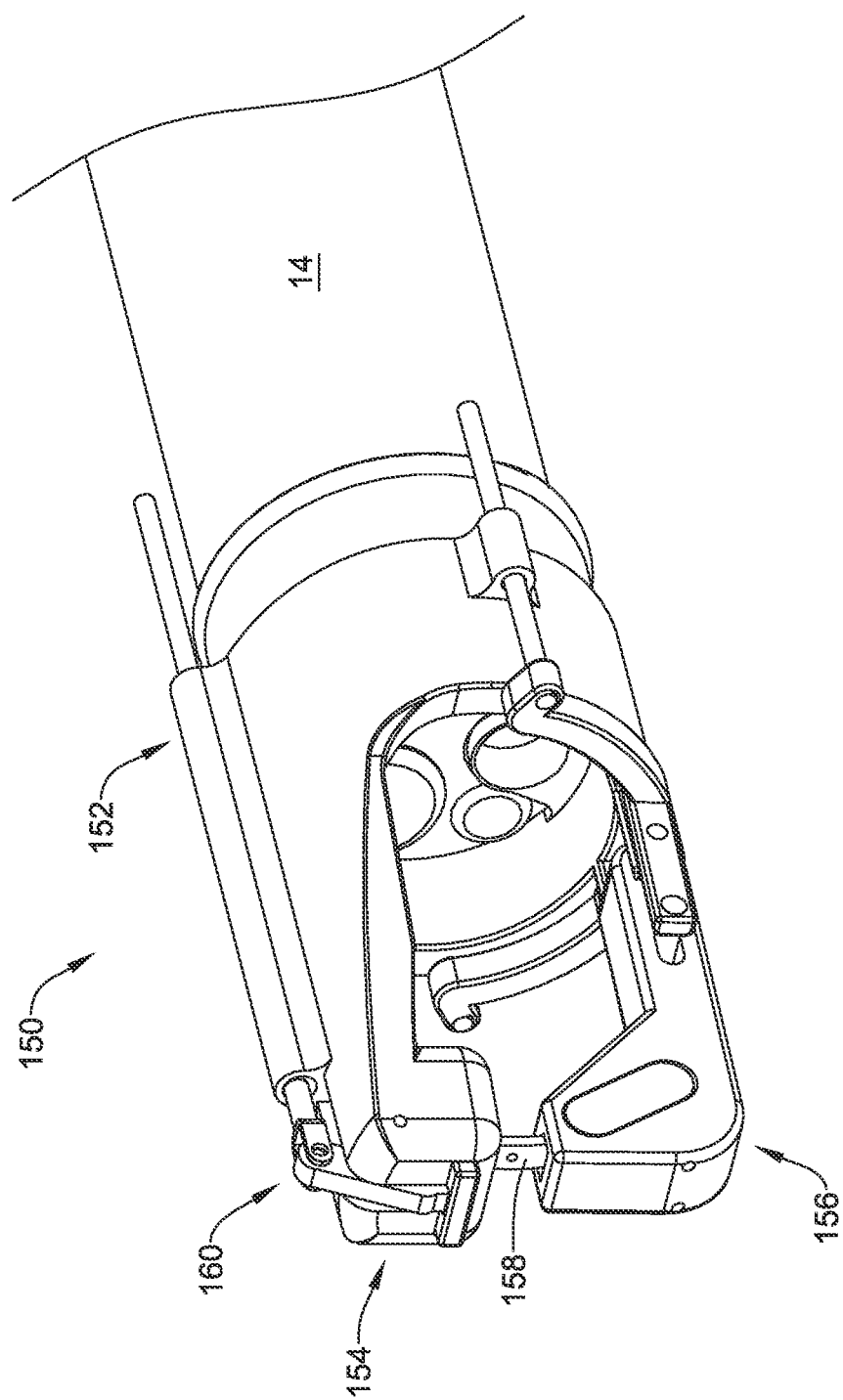
FIG. 11 is a perspective view of an illustrative assembly including an illustrative suture device secured to a distal end of an endoscope.
Figure 12:
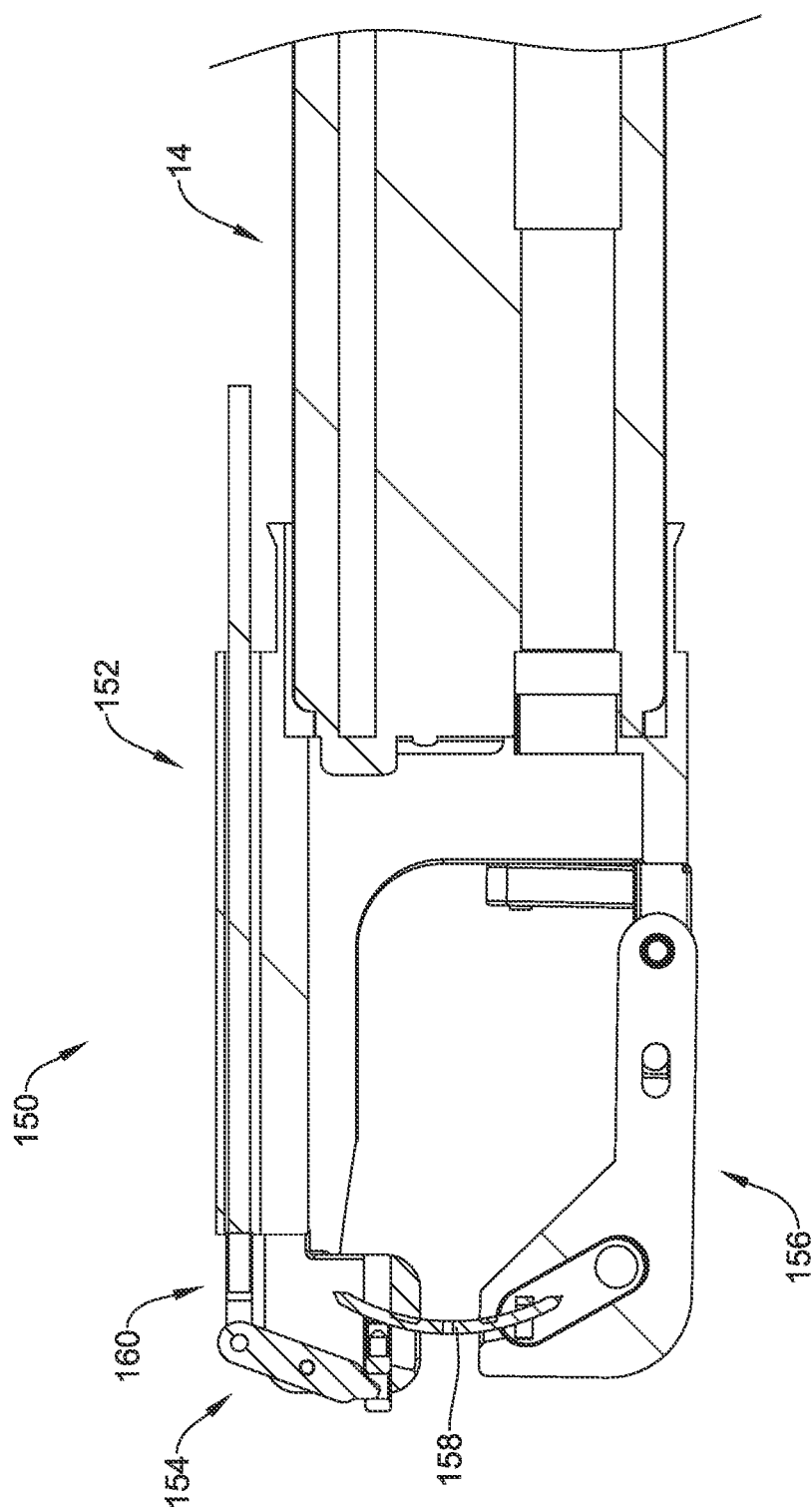
FIG. 12 is a partially cutaway side view of the illustrative assembly of FIG. 11.

FIG. 11 is a perspective view of an illustrative assembly 150 that includes an illustrative suture device 152 secured relative to the endoscope 14. FIG. 12 is a partial cross-sectional view of the illustrative assembly 150. The suture device 152 may be used in combination with a variety of different endoscopes 14, including but not limited to endoscopes 14 that have a primary working channel with a 2.8 millimeter (mm) diameter, a 3.2 mm diameter or a 3.7 mm diameter. The suture device 152 includes one static arm 154 and one moving arm 156 that may be controlled using control wires running from the moving arm 156. The control wires may pivot or swing the moving arm 156 in order to pass a needle 158 back and forth between the static arm 154 and the moving arm 156. The needle 158 may be locked to the static arm 154 via an actuating lock mechanism 160 that is controlled via a control wire by a user at the proximal end. The needle 158 may be locked to the moving arm 156 passively via a spring force. In some cases, the actuating lock mechanism 160 may be configured to provide a force that is sufficient to overcome the spring force.

It will be appreciated that a variety of different materials may be used in forming the devices described herein. In some cases, a variety of different metals may be used. Illustrative but non-limiting examples of suitable metals include titanium, stainless steel, magnesium, cobalt chromium and others. In some cases, the first control element 46 and the second control element may be made of Nitinol. In some embodiments, for example, the devices described herein may include any suitable polymeric material, including biocompatible materials such as polyurethane or silicone. Suitable polymers include PEEK (polyetheretherketone) and Polycarbonate. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A medical device, comprising:
   a mounting structure adapted to be secured to a distal end of an endoscope;
   a first suture arm pivotably secured to the mounting structure via a first pivot point, the first suture arm including:
     a first latching member at an end of the first suture arm opposing the first pivot point; and
     a first latching feature pivotably secured to the first latching member, the first latching feature pivotable with respect to the first latching member between a latching position, in which a needle is secured between and by the first latching member and the first latching feature, and a release position; and
   a second suture arm pivotably secured to the mounting structure via a second pivot point, the second suture arm including:
     a second latching member at an end of the second suture arm opposing the second pivot point; and
     a second latching feature pivotably secured to the second latching member, the second latching feature pivotable with respect to the second latching member between a latching position, in which a needle is secured between and by the second latching member, and a release position;
   wherein the second suture arm is adapted to pivot from a position about 45 degrees from vertical in an outward direction away from the first suture arm to a position about 45 degrees from vertical in an inward direction towards the first suture arm.

2. The medical device of claim 1, further comprising a first control element operably coupled to the first suture arm such that pulling on the first control element causes the first suture arm to move towards the second suture arm and pushing on the first control element causes the first suture arm to move away from the second suture arm.

3. The medical device of claim 1, further comprising a second control element operably coupled to the second suture arm such that pulling on the second control element causes the second suture arm to move towards the first suture arm and pushing on the second control element causes the second suture arm to move away from the first suture arm.

4. The medical device of claim 1, further comprising:
   a third control element operably coupled with the first latching feature in order to cause the first latching feature to move between its latching position and its release position; and
   a fourth control element operably coupled with the second latching feature in order to cause the second latching feature to move between its latching position and its release position.

5. The medical device of claim 1, further comprising:
   a first rounded pin secured relative to the first latching member and adapted to engage a latching detent of the needle when the needle is disposed between the first latching member and the first latching feature;
   a second rounded pin secured relative to the first latching feature and adapted to engage the latching detent of the needle when the first latching feature is in its latching position.

6. The medical device of claim 5, wherein the first latching member and the first latching feature together define a first lumen adapted to accept the needle when the first latching feature is in its latching position, and the first rounded pin and the second rounded pin extend partially into the first lumen.

7. The medical device of claim 1, further comprising:
   a third rounded pin secured to the second latching member and adapted to engage a latching detent of the needle when the needle is disposed between the second latching member and the second latching feature;
   a fourth rounded pin secured to the second latching feature and adapted to engage the latching detent of the needle when the second latching feature is in its latching position.

8. The medical device of claim 7, wherein the second latching member and the second latching feature in combination define a second lumen adapted to accept the needle when the second latching feature is in its latching position, and the third rounded pin and the fourth rounded pin extend partially into the second lumen.

9. The medical device of claim 1, wherein the first suture arm is adapted to pivot from a position about 45 degrees from vertical in an outward direction away from the second suture arm to a horizontal position in an inward direction towards the second suture arm.

10. The medical device of claim 9, wherein the second suture arm is adapted to permit the first suture arm to pivot through the second suture arm as the first suture arm approaches its horizontal position.

11. The medical device of claim 1, wherein the first suture arm is adapted to pivot from a position about 45 degrees from vertical in an outward direction away from the second suture arm to a position about 45 degrees from vertical in an inward direction towards the second suture arm.

12. A medical device, comprising:
   a mounting structure adapted to be secured to a distal end of an endoscope;
   a first suture arm having a proximal end pivotably secured to the mounting structure, and a distal end, the first suture arm adapted to releasably secure a needle that is adapted to puncture tissue while accommodating a suture, the first suture arm having a first width; and
   a second suture arm having a proximal end pivotably secured to the mounting structure, and a distal end, the second suture arm adapted to releasably secure the needle, the second suture arm having a second width greater than the first width such that the first suture arm is able to pivot through the second suture arm in order to capture a newly delivered needle;

where the first suture arm and the second suture arm together are adapted to pass the needle back and forth therebetween along an arcuate path; and the second suture arm is adapted to pivot from a position about 45 degrees from vertical in an outward direction away from the first suture arm to a position about 45 degrees from vertical in an inward direction towards the first suture arm.

13. The medical device of claim 12, wherein the first suture arm is adapted to pivot to a horizontal position in an inward direction towards the second suture arm with a distal end of the first suture arm adjacent the distal end of the endoscope.

14. The medical device of claim 12, wherein the first suture arm is adapted to pivot from a position about 45 degrees from vertical in an outward direction away from the second suture arm to a position about 45 degrees from vertical in an inward direction towards the second suture arm.

15. The medical device of claim 12, further comprising a first control element operably coupled to the first suture arm such that pulling on the first control element causes the first suture arm to move towards the second suture arm and pushing on the first control element causes the first suture arm to move away from the second suture arm.

16. The medical device of claim 12, further comprising a second control element operably coupled to the second suture arm such that pulling on the second control element causes the second suture arm to move towards the first suture arm and pushing on the second control element causes the second suture arm to move away from the first suture arm.

17. The medical device of claim 12, further comprising:
a third control element operably coupled with the first latching feature in order to cause the first latching feature to move between a latching position and a release position; and a fourth control element operably coupled with the second latching feature in order to cause the second latching feature to move between a latching position and a release position.

18. A medical device, comprising:
a mounting structure adapted to be secured to a distal end of an endoscope;
a first suture arm pivotably secured to the mounting structure, the first suture arm adapted to releasably secure a needle that is adapted to puncture tissue while accommodating a suture; and
a second suture arm pivotably secured to the mounting structure, the second suture arm adapted to releasably secure the needle that is adapted to puncture tissue while accommodating a suture;
wherein:
the first suture arm and the second suture arm are each actuated to move towards each other and to move away from each other in order to pass the needle back and forth therebetween along an arcuate path;
the second suture arm is adapted to pivot from a position about 45 degrees from vertical in an outward direction away from the first suture arm to a position about 45 degrees from vertical in an inward direction towards the first suture arm; and
at least one of the first suture arm or the second suture arm comprises a latching member and a latching feature pivotably secured to the latching member, the latching feature pivotable between a latching position in which a needle is secured between the latching member and the latching feature, and a release position.

19. The medical device of claim 18, wherein the first suture arm is adapted to pivot to a horizontal position in a inward direction towards the second suture arm with a distal end of the first suture arm adjacent the distal end of the endoscope.

20. The medical device of claim 18, wherein the first suture arm is adapted to pivot from a position about 45 degrees from vertical in an outward direction away from the second suture arm to a position about 45 degrees from vertical in an inward direction towards the second suture arm.

* * * * *